(12) United States Patent
Zimmerman et al.

(10) Patent No.: US 10,339,563 B1
(45) Date of Patent: Jul. 2, 2019

(54) METHOD AND APPARATUS OF PROVIDING MESSAGING TO TARGETED LIFESTYLE SEGMENTS

(75) Inventors: Scott W. Zimmerman, Fairhope, AL (US); Corey K. DeGeorge, Mobile, AL (US)

(73) Assignee: WEST CORPORATION, Omaha, NE (US)

( * ) Notice: Subject to any disclaimer, the term of this patent is extended or adjusted under 35 U.S.C. 154(b) by 728 days.

(21) Appl. No.: 13/276,444

(22) Filed: Oct. 19, 2011

(51) Int. Cl.
*G06Q 30/02* (2012.01)
*G16H 10/60* (2018.01)
*H04M 11/00* (2006.01)

(52) U.S. Cl.
CPC ......... *G06Q 30/0255* (2013.01); *G16H 10/60* (2018.01)

(58) Field of Classification Search
CPC ............................ G16H 10/60; G06Q 30/0255
USPC .......................................................... 705/2–3
See application file for complete search history.

(56) References Cited

U.S. PATENT DOCUMENTS 5,926,526 A * 7/1999 Rapaport et al. .......... 379/88.25
2006/0259329 A1* 11/2006 Kline ................................ 705/3

* cited by examiner

*Primary Examiner* — Elaine Gort
*Assistant Examiner* — Rachelle L Reichert
(74) *Attorney, Agent, or Firm* — Raffi Gostanian

(57) ABSTRACT

A method and apparatus of processing pre-stored recipient information and configuring a targeted message to be sent to the recipient(s) is disclosed. One example method of operation includes retrieving a list of recipients and corresponding recipient profile information from a database, and comparing the recipient profile information to at least one target lifestyle segment or persona (e.g., demographics, healthcare spending, consumer spending, and media preferences). The method may also include identifying that the list of intended recipients' profile information matches the target persona, and selecting and transferring a pre-recorded, persona-tailored automated voice call script to the list of recipients according to a minimum response threshold value of the target persona.

18 Claims, 5 Drawing Sheets

US 10,339,563 B1

METHOD AND APPARATUS OF PROVIDING MESSAGING TO TARGETED LIFESTYLE SEGMENTS

TECHNICAL FIELD OF THE INVENTION

This invention relates to a method and apparatus of identifying various lifestyle segment or cluster groups based on demographic, healthcare spending, consumer spending, and media preferences, and then executing a messaging strategy to transmit targeted messaging and related content to the identified persona.

BACKGROUND OF THE INVENTION

Healthcare services continuously rely on the capability to communicate with the end users/patients regarding their ongoing health problems, concerns, and routine checkups. It is a challenge for health care entities (HCEs) to contact patients/guarantors/members, etc., or for businesses to contact their customers.

In certain circumstances, merely sending a letter, e-mail and/or calling the patients or customers on the phone are not sufficient to ensure that important information has been communicated. For example, a HCE may desire to contact a patient regarding payment of a bill, scheduling an appointment, tracking healthcare behavior, etc. Different cluster groups or lifestyle segments (e.g., age, generational type, level of education, marital status, household income, occupation, housing type, race, presence of children, media preferences, consumer spending, etc.) behave and respond differently from one another.

SUMMARY OF THE INVENTION

One example embodiment of the present invention may include a method that includes retrieving a list of recipients and corresponding recipient profile information from a database and comparing the recipient profile information to at least one target persona. The method may also include identifying that the list of intended recipients' profile information matches the target persona and selecting and transferring a pre-recorded automated voice call script to the list of recipients according to a minimum response threshold value of the target persona.

Another example embodiment of the present invention includes an apparatus that includes a data retrieval engine configured to retrieve a list of recipients and corresponding recipient profile information from a database and a data analytics engine configured to compare the recipient profile information to at least one target persona, and to identify that the list of intended recipients' profile information matches the target persona. The apparatus may also include a data reporting engine configured to select and transfer a pre-recorded automated voice call script to the list of recipients according to a minimum response threshold value of the target persona.

DETAILED DESCRIPTION OF THE INVENTION

It will be readily understood that the components of the present invention, as generally described and illustrated in the figures herein, may be arranged and designed in a wide variety of different configurations. Thus, the following detailed description of the embodiments of a method, apparatus, and system, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present invention. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" has been used in the description of embodiments of the present invention, the invention may be applied to many types of network data, such as packet, frame, datagram, etc. For purposes of this invention, the term "message" also includes packet, frame, datagram, and any equivalents thereof. Furthermore, while certain types of messages and signaling are depicted in exemplary embodiments of the invention, the invention is not limited to a certain type of message, and the invention is not limited to a certain type of signaling.

Example embodiments of the present invention include organizing different lifestyle segments and tracking their respective behavior. Different personas may display a user's desired contact preferences based on their historical behavior gathered from previous calls or communication sessions. A messaging strategy for contacting users of a particular persona may include a combination of message content, message structure, voice gender, voice dialect, tone of voice, message length, time the message is sent, frequency of message delivery, and channel of communication (e.g., cell phone text messaging, push notification, e-mail, phone call, video, etc.).

Figure 1:
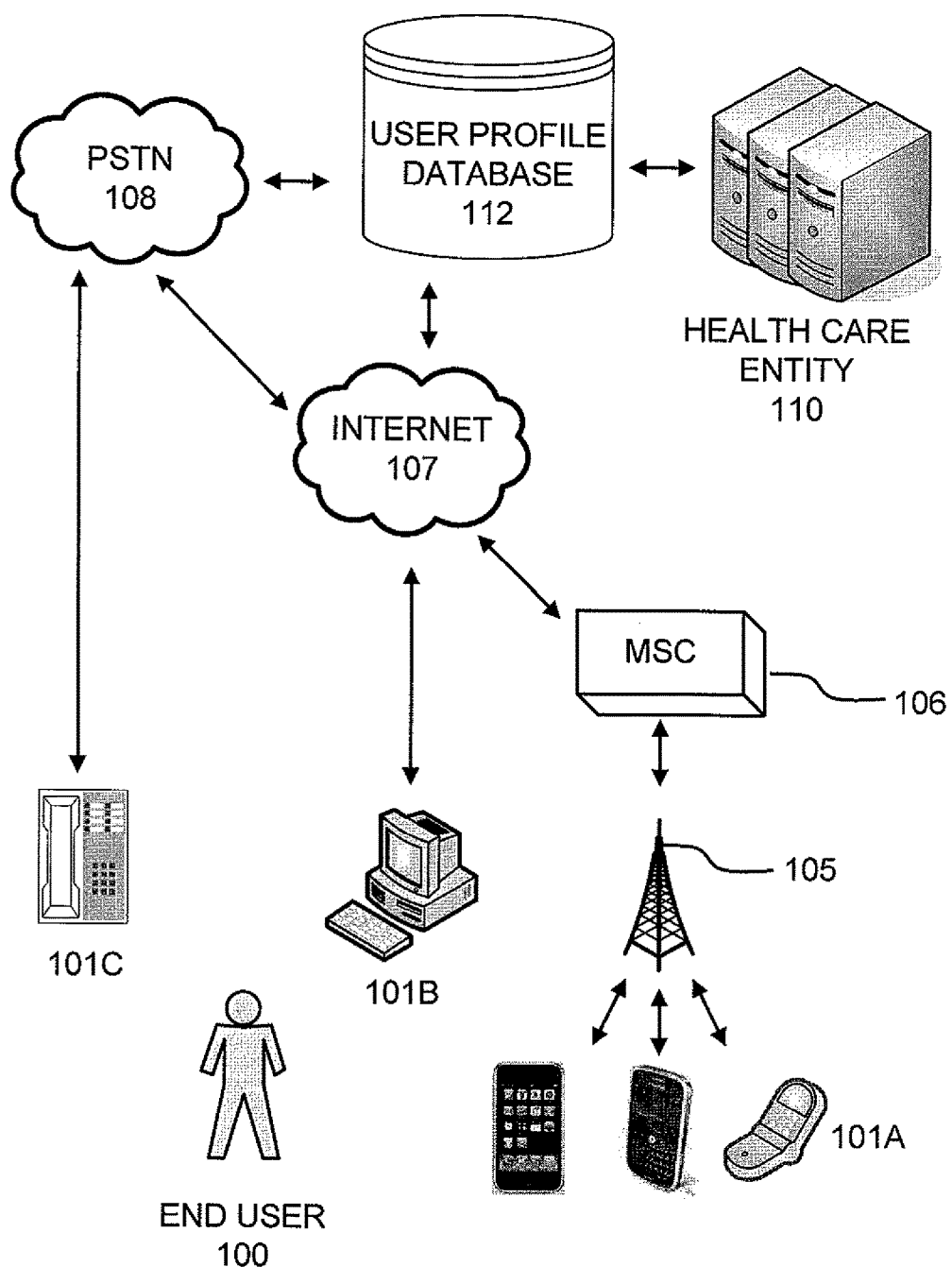
FIG. 1 illustrates an example network configuration according to example embodiments of the present invention

FIG. 1 illustrates an example network configuration according to example embodiments of the present invention. Referring to FIG. 1, the end user 100 may have access to any mobile station 101A, desktop PC device 101B, such as, a cell phone, Blackberry®, iPhone®, or other type of smartphone, desktop or laptop communication device. The end user 100 may also have access to a regular landline telephone 101C. The mobile station 101A may be used to communicate to a base station 105 via a wireless communication signal, which, in turn, communicates to a regional mobile switching center (MSC) 106. The MSC 106 will relay data messages, voice calls, etc., across the Internet 107 to a destination, such as the health care entity 110 and/or the user profile database 112.

Alternatively, the end user 100 may be contacted via a personal computer 101B that connects to the Internet 107 to provide voice calls, e-mail services, etc. The end user 100 may also be contacted by a telephone 101C that connects to the PSTN 108. The user profile database 112 may be a third party database that contains user profile persona information requested by the health care entity 110. In another example, the health care entity (HCE) 110 may maintain, update and retrieve data from its own user profile database 112.

Figure 2:
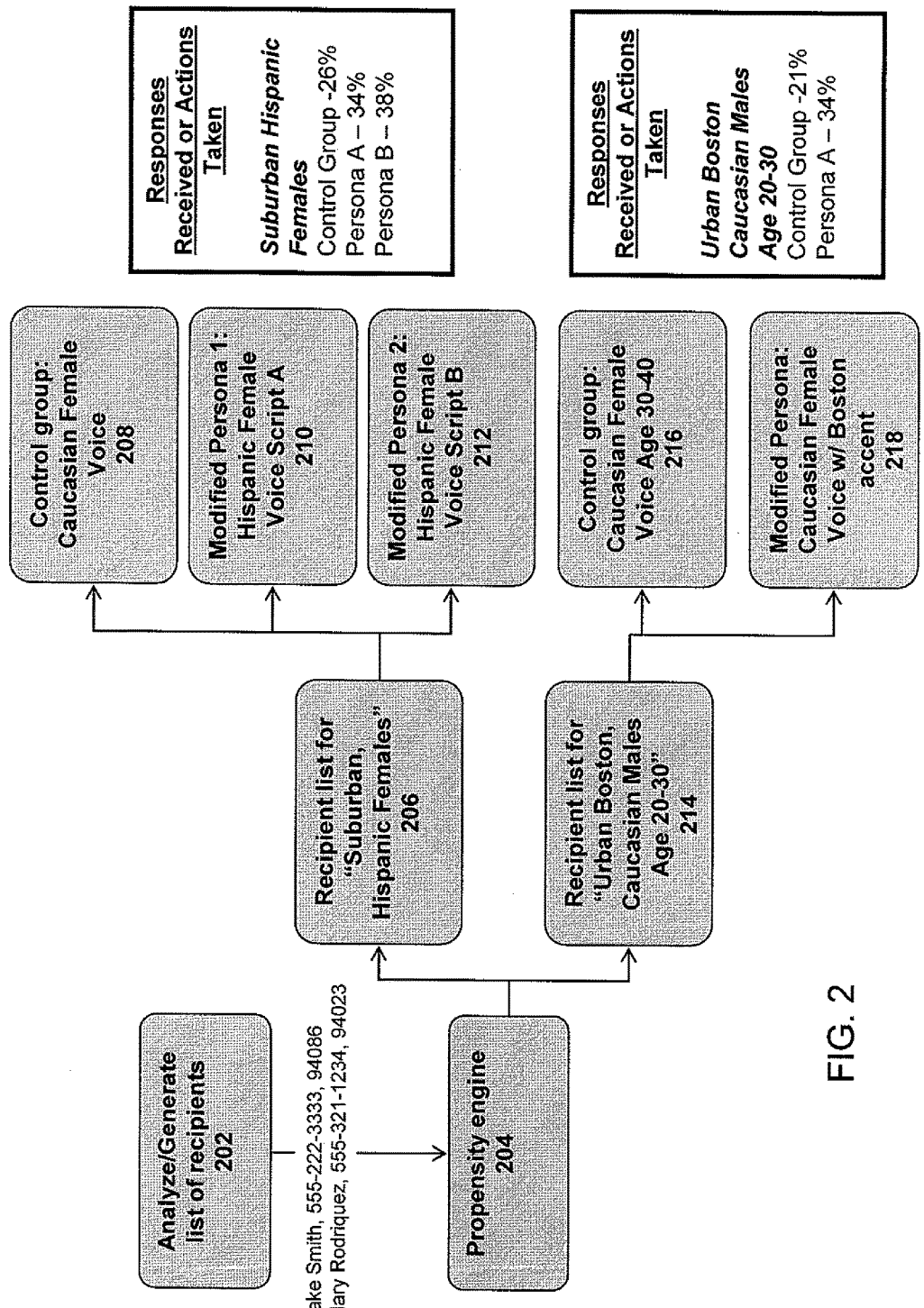
FIG. 2 illustrates a logic diagram of a targeted communication procedure based on one or more user persona according to example embodiments of the present invention.

FIG. 2 illustrates a logic diagram of a targeted communication procedure based on lifestyle segments according to example embodiments of the present invention. Referring to FIG. 2, a list of known recipients are extracted and generated 202 from a user profile database 112 by the health care entity 110. The recipients may represent patients whose personal information, medical records, etc. have been previously submitted and/or entered into the patient profile system of the health care entity 110. The list of recipients may be identified by basic user information, such as username, address, telephone number, social security number, etc. Certain portions of the user's basic profile information may be extracted to calculate a persona, which may include a lifestyle segment profile used to contact one or more of the patients.

The generated list of recipients 202 are forwarded to a propensity engine 204 which takes the user profile information and compares it to historic persona information based on any of the above-note profile information. Examples of persona information used to identify a person, group of people, or related entities may include information categories, such as age, generational type, level of education, marital status, household income, occupation, housing type, race, presence of children, media preferences, consumer spending, etc. Although suspect categories, such as race or household income have been named as examples of persona categories, such persona categories are not used to limit assistance but to promote proactive assistance to users regardless of the persona used. Certain users included on the generated list of recipients 202 may fit into a predetermined persona profile. For example, Mary Rodriguez may be profiled according to her name, age and street address or zip code as a suburban Hispanic female 206. Jake Smith may be identified as an intended recipient for an urban Boston Caucasian male 214 between the ages of 20-30. At this point, it may be discerned from historic persona data that these two recipients are best suited for different automated call personas (e.g., virtual agents).

In a test mode of operation, the automated call system logic may create two different groups of persona profiles to test against various call agents or virtual call agents (automated call agents). The suburban Hispanic females may be broken up into three groups of a dozen or more identified recipients. The first group may be contacted by a Caucasian female voice group 208, the second group by a modified persona 210 Hispanic female following a first voice script A and the last group may be contacted by another modified persona 212 Hispanic female following a second voice script B different from the first voice script. The voice scripts may be read by live agents or may be based on a pre-recorded voice.

Similar to the first example, the second recipient list may be organized into an urban Caucasian male profile between the ages of 20-30 214. This test may be conducted to determine the response feedback according to two different strategies. The first call strategy is a control group that is greeted with a Caucasian female voice 216 between the ages of 30-40. The modified persona may include additional personalization considerations, such as a Caucasian female voice with a Boston accent 218. The rightmost portion of FIG. 2 illustrates the results of these actions. The responses received from the suburban Hispanic females were highest with respect to the female voice script B. The responses received from the urban Boston males ages 20-30 were highest for the female voice with the Boston accent. The data may be recorded and iteratively used for future calling efforts to secure higher feedback response ratios.

Figure 3:
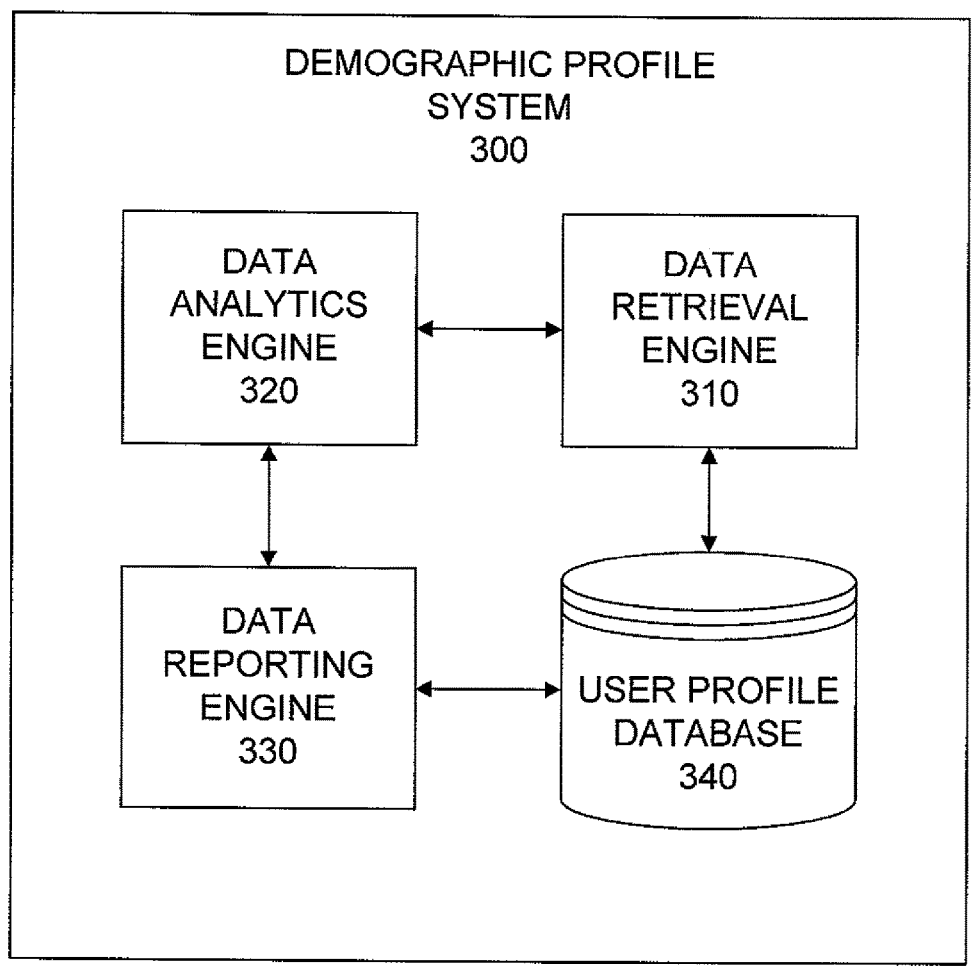
FIG. 3 illustrates an example of user persona information processing system according to example embodiments of the present invention.

FIG. 3 illustrates an example persona categorization processing system according to example embodiments of the present invention. Referring to FIG. 3, the user persona profile system 300 may analyze the effectiveness of message strategies according to various lifestyle elements (e.g., age, generational type, level of education, marital status, household income, occupation, housing type, race, presence of children, media preferences, consumer spending, etc.). The message strategy may include but is not limited to the message content, message structure, voice gender, voice dialect, tone of voice, message length, time the message is sent, frequency of the message or series of messages, and the channel of communication (e.g., cell phone text messaging, push notification, e-mail, phone call, video, etc.). Based on the messaging strategies that the system has determined are most effective for a particular persona group, message campaigns in an automated messaging system can be automatically tailored to utilize the optimized strategy for each particular group of individuals (i.e., lifestyle segments or clusters).

According to one example method of operation, the system may retrieve a list of contact information via a data retrieval engine 310 for a group of people intended to be contacted. A persona profile analysis is performed by the data analytics engine 320 to match each of the records in the list to a persona profile (e.g., members of a zip code 12345-2222). The street addresses or zip codes may be identified by a particular lifestyle segment parameter profile, such as, age median, geographic location, dominant ethnicity, median income level, accent spoken, etc. The street address or zip code may be associated with one or more of the above-noted personas.

The persona profile system 300 may be required to operate in communication mode (e.g., live mode) to retrieve persona elements and begin calling, text messaging, e-mailing, the intended recipients to inform them of their routine health care information, etc. In another mode of operation, the system 300 may operate in test mode to determine the type of feedback received from a particular persona so future contact attempts will be based on causal information that provides a predictive and anticipatory analysis for subsequent contact attempts. The system may include a memory, transmitter, receiver, processor (not shown) used to drive any of the various engines.

Assuming for this example, the system 300 is operating in test mode, the system 300 will automatically separate the list of people in that group into separate random lists to perform testing on various message strategies. The automated messaging system will execute each messaging strategy, such as control strategies and one or more experimental strategies. The system 300 may receive additional data from an outside and/or remote information source indicating which members/customers of a particular persona performed which actions during a predefined period of time. For example, a certain sub-element (e.g., males ages 20-30) of a particular persona, zip code 12345-2222 may respond in a particular manner to a particular message type, format or information request. Another example may be based on five members of a predefined persona performing a credit card payment during a particular time frame, in response to a particular message type, etc.

The system 300 may refer to the responses, feedback, payments received, and a lack thereof to compile an effectiveness rating of each message strategy. A messaging strategy may be based on a message type (e.g., phone call, e-mail, text message, live call, automated call, etc.) and may include additional strategies, such as tone, accent, message duration, additionally presented user options, etc. A report of the messaging strategy may be generated via a data reporting engine 330 and displayed in a graph format on a data analyst dashboard, or simply used to update a spreadsheet stored in the user profile database 112. The reports may be based on particular persona groups that were tested while operating in test mode. The test mode may simultaneously be a live mode except that feedback and response data is tracked and analyzed by the data processing system 300.

Once a test is completed and the data results are compiled, the automated messaging system may then refer to the test results to implement the most effective strategy the next time a persona message campaign is created and sent to a particular cluster. One example may include a health care provider sending recall messages to corresponding patients. In this example, a list of patients due for the recall (e.g., a drug previously prescribed to those patients must now be stopped immediately due to an FDA recall) must be contacted immediately to inform them of the drug recall. A notification message must be generated and sent to each of the users via the data reporting engine 330.

Initially, a list is compiled of all the names of those individuals who are taking the recalled drug via the data retrieval engine. Next, a communication channel preference is noted for each of the users and sub-groups are formed to notify the users via their preferred communication medium and based on compiled persona information used to predict the preferred communication channel via the data analytics engine 320 (e.g., cell phone, automated voice mail, home phone, text message, e-mail, etc.). The notification and data reporting engine 330 may transmit a message to various different communication engines operated by the channel carriers (e.g., PSTN, Internet/e-mail server, cellular communication centers, etc.) needed to deliver the messages securely to each of the intended recipients, such as a message queue of a mobile application. For this specific communication medium example, the mobile application then delivers a push notification to notify the recipients of the recall. Confirmation may be required to stop the notifications from repeating. The end user 100 may observe a virtual button in the e-mail and select the button to provide a confirmation that the message was received and understood.

The mobile application may also provide multimedia communication, such as text, audio, graphics, video, etc., for the user to receive more data regarding the message. According to another example, a less urgent message may be created to inform all diabetic patients why a retinal exam is critical for those who either have diabetes or are at high risk of developing diabetes. The message may be compiled as a convincing video developed by a panel of doctors who have compelling evidence that eye problems are linked to diabetes, and that a retinal exam is easy to conduct and usually covered by insurance. The video link may be created and linked to a list of diabetic or high-risk patients stored in the user profile database 112. A corresponding message may be created and sent to those patients according to the preferences and history of their user persona.

The end user 100 may receive an e-mail, text message or other form of communication including a hyper-link indicating the intended video data. The end user 100 may also receive a summary and message indicating the conclusive data of the video along with options to confirm that the message has been received and the purpose has been understood by the recipient end user 100.

According to one example method of operation, a list of intended recipients may be retrieved from the user profile database 112. The corresponding recipient profile information may also be retrieved from the database 112 and compared to a target persona that will be used to transfer messages to one or more of the recipients. The list of intended recipients may be further limited by comparing the target lifestyle segment (e.g., age, generational type, level of education, marital status, household income, occupation, housing type, race, presence of children, media preferences, consumer spending, etc.) to the actual user profile information retrieved from the database 112. Those users who match the target persona will be sent a pre-recorded, persona-tailored automated voice call script. The selection of the voice call script may be based on a voice call script that has a minimum response threshold value associated with the target cluster group and/or persona (e.g., 75% or more positive feedback indications). The minimum response threshold value may be previously determined based on one or more test modes of operation performed on various personas. The voice call scripts may be numerous and those that have the greatest response percentages for a particular persona will be used again for that particular persona.

The recipients may be identified as patients whose personal information and medical records have been previously stored in the database 112. The recipients may be identified by their name, address, telephone number, and social security number, etc. The target persona may be selected according to a street address, zip code, recipient age range, recipient gender, recipient race, recipient language preference, recipient income level, or other persona elements included elsewhere in this disclosure. The present contact efforts may be conducted by a voice call that is sent to a user's mobile station 101A or landline 101C. The outcome of the voice calls may be identified as a current response value based on recipient feedback from the transferred pre-recorded automated voice call. For example, the end users may respond to certain questions or prompts generate by the pre-recorded automated voice call. The total number of responses may be identified for each recipient among the various recipients, and an average may be computed to calculate the mean, median or range of successful responses generated by the recipients. This value may be used to update the minimum response threshold value of the targeted persona for future reference.

The target persona may be paired with one or more of the pre-recorded automated voice call scripts. The voice call script may be selected for the target persona based on a combination of message content, message structure, voice gender, voice dialect, tone of voice, message length, time the message is sent, frequency of message delivery, and channel of communication (e.g., cell phone text messaging, push notification, e-mail, phone call, video, etc.). The message(s)

may be sent to the recipients based on user preferences and/or the preferred channel identified for the persona.

The operations of a method or algorithm described in connection with the embodiments disclosed herein may be embodied directly in hardware, in a computer program executed by a processor, or in a combination of the two. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example FIG. 4 illustrates an example network element 400, which may represent any of the above-described network components of FIGS. 1-3.

Figure 4:
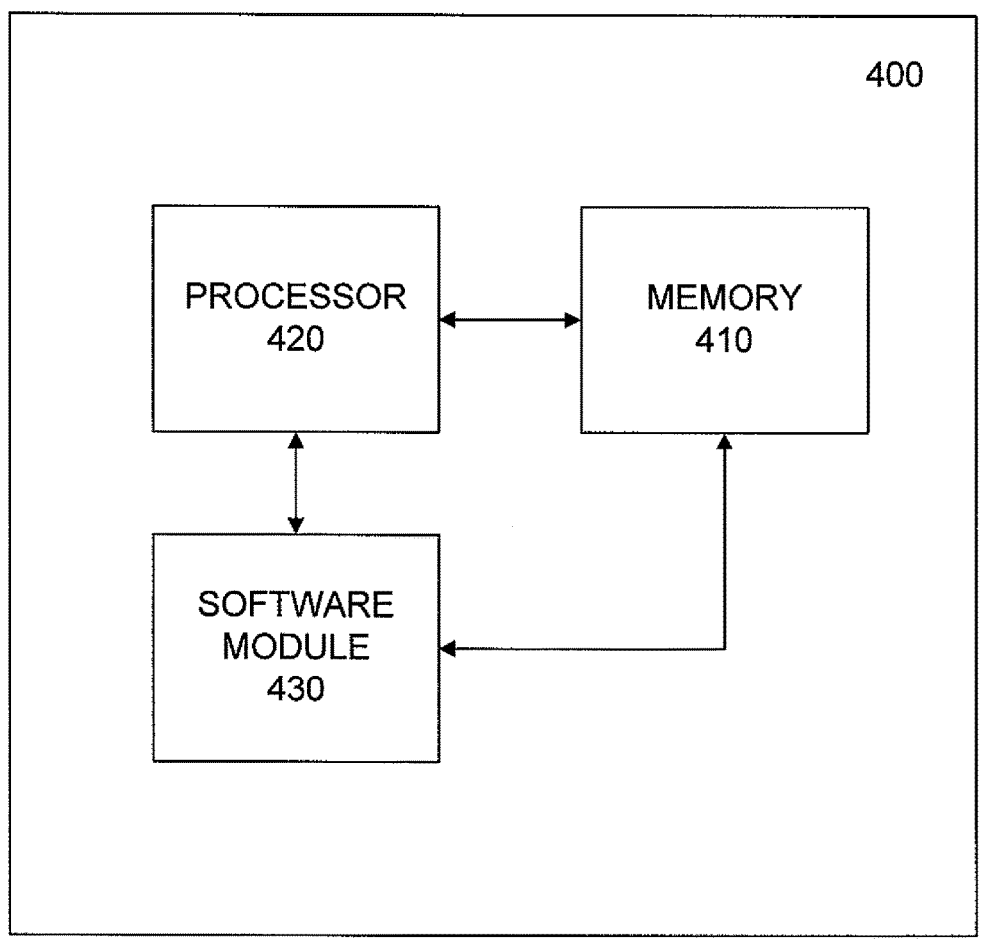
FIG. 4 illustrates a network entity that may include memory, software code and other computer processing hardware, and which may be configured to perform operations according to example embodiments of the present invention.

As illustrated in FIG. 4, a memory 410 and a processor 420 may be discrete components of the network entity 400 that are used to execute an application or set of operations. The application may be coded in software in a computer language understood by the processor 420, and stored in a computer readable medium, such as, the memory 410. Furthermore, a software module 430 may be another discrete entity that is part of the network entity 400, and which contains software instructions that may be executed by the processor 420. In addition to the above noted components of the network entity 400, the network entity 400 may also have a transmitter and receiver pair configured to receive and transmit communication signals (not shown).

Figure 5:
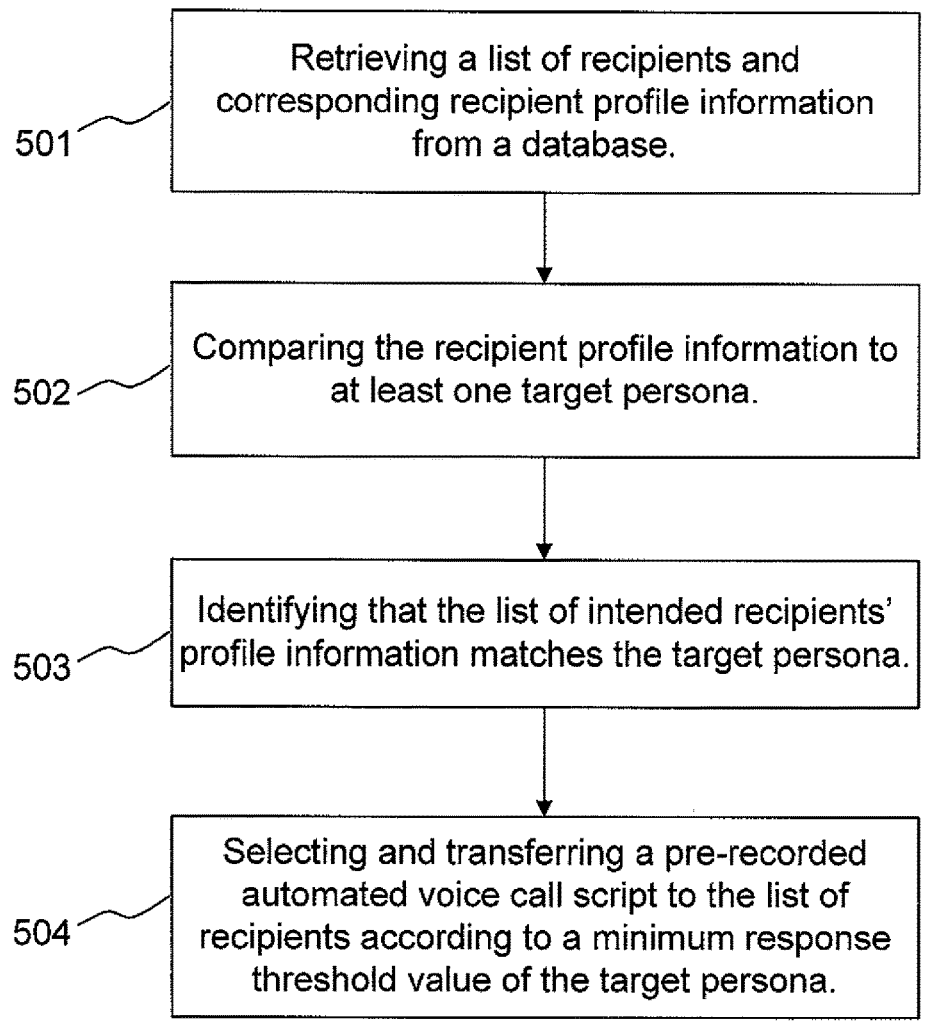
FIG. 5 illustrates a flow diagram of an example method of operation according to example embodiments of the present invention.

One example embodiment of the present invention may include a method as illustrated in the flow diagram of FIG. 5. The method may include retrieving a list of recipients and corresponding recipient profile information from a database, at operation 501, comparing the recipient profile information to at least one target persona, at operation 502, identifying that the list of intended recipients' profile information matches the target persona, at operation 503 and selecting and transferring a pre-recorded automated voice call script to the list of recipients according to a minimum response threshold value of the target persona, at operation 504. The recipients may be easily contacted to share any type of information associated with the data processing entity configured to initiate communication with the recipients of the persona.

While preferred embodiments of the present invention have been described, it is to be understood that the embodiments described are illustrative only and the scope of the invention is to be defined solely by the appended claims when considered with a full range of equivalents and modifications (e.g., protocols, hardware devices, software platforms etc.) thereto.

What is claimed is:

1. A method comprising: retrieving a list of recipients and corresponding recipient profile information from a database; comparing, via a processor, the recipient profile information to at least one target persona profile comprising a plurality of demographic elements stored in memory; identifying at least a portion of the list of intended recipients' profile information matches the target persona profile by comparing and matching a majority of the plurality of demographic elements of the target persona profile to a corresponding majority of a plurality of demographic elements identified from the list of intended recipients' profile information; selecting a matching portion of the list of recipients as the portion of the list of recipients which will receive a pre-recorded automated voice call script; selecting the pre-recorded automated voice call script that has a minimum response threshold value as a numerical percentage value representing pre-stored positive response feedback information received in a previously conducted communication session from the matching portion of the list of recipients; and transferring, via a transmitter, the pre-recorded automated voice call script to the matching portion of the list of recipients, wherein content of the pre-recorded automated voice call is transferred to one or more of the intended recipients by at least one of e-mail, text messaging, and social networking communications based on the predefined recipient preferences stored in the database.

2. The method of claim 1, wherein the recipients are patients whose personal information and medical records have been previously stored in the database.

3. The method of claim 1, wherein the recipients may be identified by at least one of name, address, telephone number, and social security number.

4. The method of claim 1, wherein the plurality of demographic elements comprises at least two of an address, a zip code, a recipient age range, a recipient gender, a recipient race, a recipient language preference, and a recipient income level.

5. The method of claim 1, further comprising:
identifying a current response value based on recipient feedback from the transferred pre-recorded automated voice call; and
updating the minimum response threshold value of the target persona profile based on the current response value.

6. The method of claim 1, wherein the transferred pre-recorded automated voice call is selected for the target demographic based on one or more of voice, dialect, message length, time of day the message is sent, and a channel of communication used to transfer the message.

7. An apparatus comprising: a memory; a processor configured to retrieve a list of recipients and corresponding recipient profile information from a database; compare the recipient profile information to at least one target persona profile comprising a plurality of demographic elements stored in the memory; identify at least a portion of the list of intended recipients' profile information matches the target demographic persona profile by a comparison and match of a majority of the plurality of demographic elements of the target persona profile to a corresponding majority of a plurality of demographic elements identified from the list of intended recipients' profile information; select a matching portion of the list of recipients as the portion of the list of recipients which will receive a pre-recorded automated voice call script; select the pre-recorded automated voice call script that has a minimum response threshold value as a numerical percentage value representing pre-stored positive response feedback information received in a previously conducted communication session from the matching portion of the list of recipients; and a transmitter configured to transfer the pre-recorded automated voice call script to the matching portion of the list of recipients, wherein content of the pre-recorded automated voice call is transferred to one or more of the intended recipients by at least one of e-mail, text messaging, and social networking communications based on the predefined recipient preferences stored in the database.

8. The apparatus of claim 7, wherein the recipients are patients whose personal information and medical records have been previously stored in the database.

9. The apparatus of claim 7, wherein the recipients may be identified by at least one of name, address, telephone number, and social security number.

10. The apparatus of claim 7, wherein the plurality of demographic elements comprises at least two of an address, a zip code, a recipient age range, a recipient gender, a recipient race, a recipient language preference, and a recipient income level.

11. The apparatus of claim 7, wherein the processor is further configured to
identify a current response value based on recipient feedback from the transferred pre-recorded automated voice call; and
update the minimum response threshold value of the target persona profile based on the current response value.

12. The apparatus of claim 7, wherein the transferred pre-recorded automated voice call is selected for the target demographic based on one or more of voice, dialect, message length, time of day the message is sent, and a channel of communication used to transfer the message.

13. A non-transitory computer readable storage medium configured to store instructions that when executed cause a processor to perform: retrieving a list of recipients and corresponding recipient profile information from a database; comparing the recipient profile information to at least one target persona profile comprising a plurality of demographic elements stored in memory; identifying at least a portion of the list of intended recipients' profile information matches the target persona profile by comparing and matching a majority of the plurality of demographic elements of the target persona profile to a corresponding majority of a plurality of demographic elements identified from the list of intended recipients' profile information; selecting a matching portion of the list of recipients as the portion of the list of recipients which will receive a pre-recorded automated voice call script; selecting the pre-recorded automated voice call script that has a minimum response threshold value as a numerical percentage value representing pre-stored positive response feedback information received in a previously conducted communication session from the matching portion of the list of recipients; and transferring the pre-recorded automated voice call script to the matching portion of the list of recipients, wherein content of the pre-recorded automated voice call is transferred to one or more of the intended recipients by at least one of e-mail, text messaging, and social networking communications based on the predefined recipient preferences stored in the database.

14. The non-transitory computer readable storage medium of claim 13, wherein the recipients are patients whose personal information and medical records have been previously stored in the database.

15. The non-transitory computer readable storage medium of claim 13, wherein the recipients may be identified by at least one of name, address, telephone number, and social security number.

16. The non-transitory computer readable storage medium of claim 13, wherein the plurality of demographic elements comprises at least two of an address, a zip code, a recipient age range, a recipient gender, a recipient race, a recipient language preference, and a recipient income level.

17. The non-transitory computer readable storage medium of claim 13, wherein the processor is further configured to perform:
identifying a current response value based on recipient feedback from the transferred pre-recorded automated voice call; and
updating the minimum response threshold value of the target persona profile based on the current response value.

18. The non-transitory computer readable storage medium of claim 13, wherein the transferred pre-recorded automated voice call is selected for the target demographic based on one or more of voice, dialect, message length, time of day the message is sent, and a channel of communication used to transfer the message.

* * * * *